United States Patent [19]

Schmer

[11] 4,431,428
[45] Feb. 14, 1984

[54] BIO-ARTIFICIAL ORGAN USING MICROENCAPSULATED ENZYMES

[75] Inventor: Gottfried Schmer, Seattle, Wash.

[73] Assignee: Trimedyne, Inc., Arlington Heights, Ill.

[21] Appl. No.: 306,910

[22] Filed: Sep. 30, 1981

[51] Int. Cl.³ .............................................. A61M 7/00
[52] U.S. Cl. ..................................... 604/897; 604/890
[58] Field of Search ............................ 424/22, 16, 32; 604/890, 891, 892, 897; 128/1 R, 130; 3/1

[56] References Cited

U.S. PATENT DOCUMENTS

| | | |
|---|---|---|
| 3,996,934 | 12/1976 | Zaffaroni ............................ 604/897 |
| 4,327,710 | 5/1982 | De Loach et al. .................. 128/1 R |
| 4,351,337 | 9/1982 | Sidman .................................. 424/22 |
| 4,353,888 | 10/1982 | Sefton .................................... 424/32 |

*Primary Examiner*—C. Fred Rosenbaum
*Assistant Examiner*—T. J. Wallen

[57] ABSTRACT

A bio-artificial organ containing a biochemically active matrix is disclosed. The biochemically active matrix includes biochemically active enzyme-containing microcapsules entrapped within a gel matrix. An extracorporeal blood flow can be passed through the organ and over the biochemically active matrix to permit the enzyme to perform its enzymatic function on a substrate in the blood.

12 Claims, 4 Drawing Figures

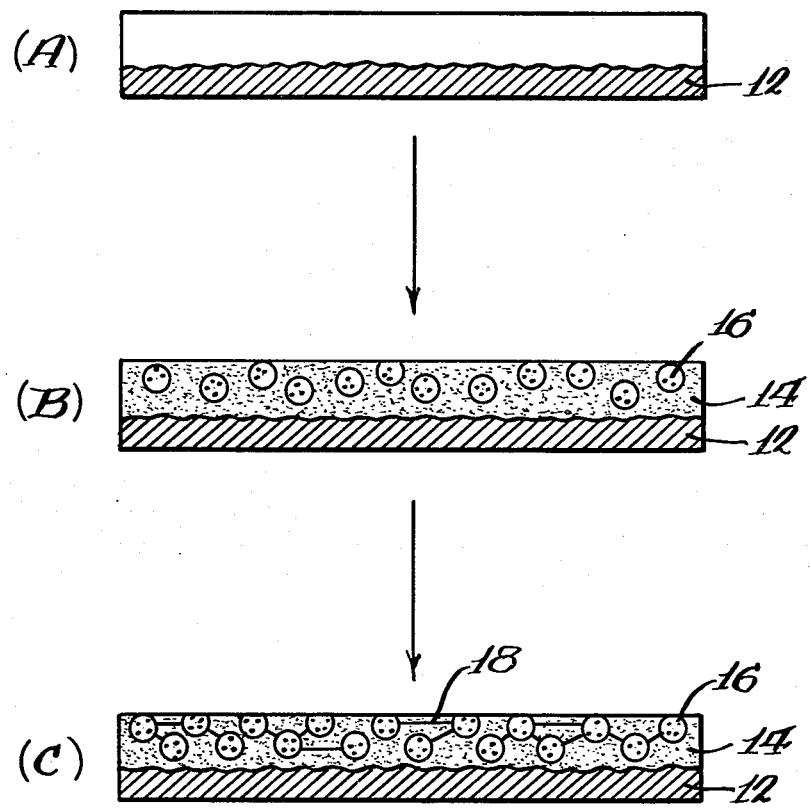
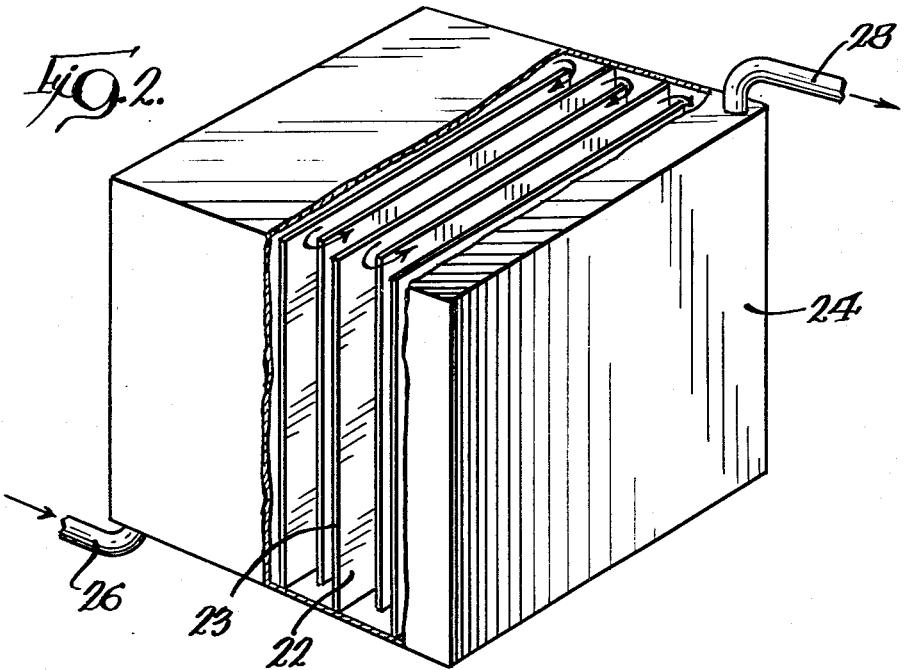

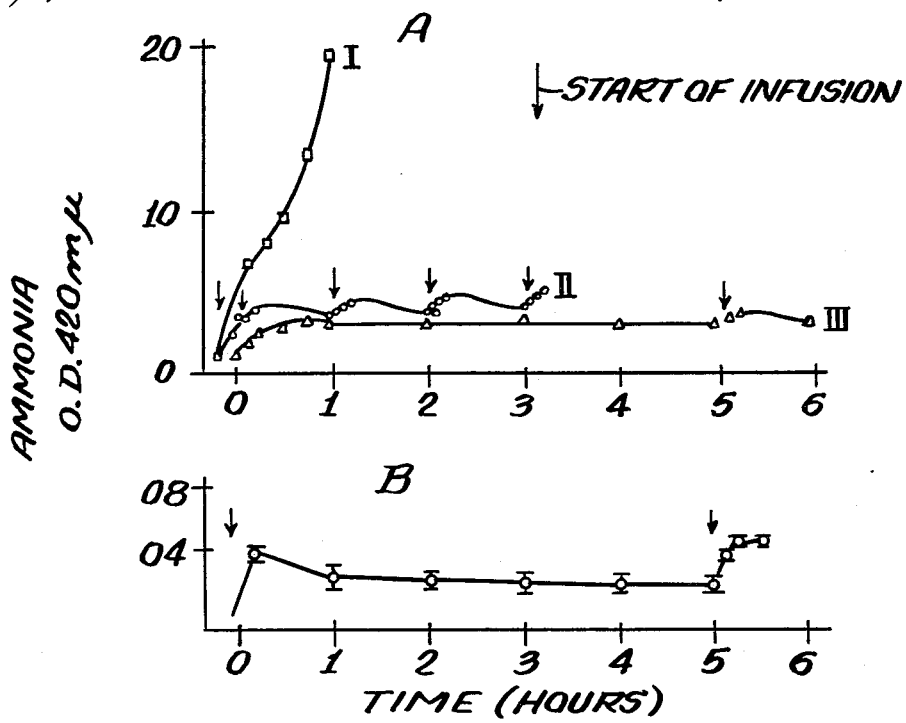
Fig. 3. IN VIVO TESTING OF UREASE-RED CELL GHOST ORGAN
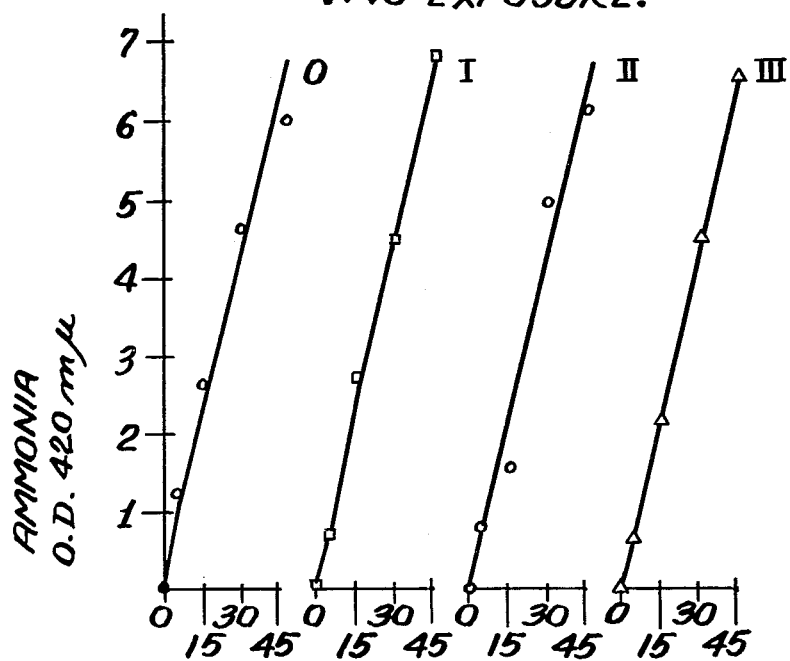
Fig. 4. IN VITRO TESTING OF UREASE-RED CELL GHOST ORGAN BEFORE (0) AND AFTER (I, II, III,) EACH IN VIVO EXPOSURE.

BIO-ARTIFICIAL ORGAN USING MICROENCAPSULATED ENZYMES

TECHNICAL FIELD

This invention relates to bio-artificial organs and in particular bio-artificial organs utilizing microencapsulated biochemically active enzymes.

BACKGROUND OF THE INVENTION

In recent years, it has been shown that enzymes can be used to alleviate certain disorders of the blood by reducing the amount of a particular substrate within the blood. The blood is contacted with an enzyme which degrades the substrate whose concentration it is desirable to reduce. However, the administration of an enzyme to a patient by injection into the blood stream of the patient makes control of the total enzyme activity difficult because it is impossible to limit the time period during which the enzyme acts on the substrate. In addition, certain free enzymes have toxic side effects making injection difficult or unfeasible.

To avoid these toxic side effects, many attempts have been made to immobilize the enzyme on an insoluble support and then pass an extracorporeal blood flow over this support. This approach seeks to permit the enzyme to act on the substrate while preventing release of the enzyme into the blood stream and the accompanying undesirable side effects.

Attempts made in the past to immobilize biochemically active enzymes on or within various types of support materials have met with varying degrees of success. Among the problems encountered are short shelf life for the support-bound enzyme, leakage of enzyme from the support, a low enzyme holding capacity for certain supports, incompatibility with a blood flow because of such problems as platelet aggregations, and reduced enzyme activity because of excessive bonding to the enzyme or interference of substrate and enzyme product flow through the support. Excessive activation of the support by a linking agent increases the probability of multiple site bonding on the enzymes which quite frequently results in substantial deactivation of the enzyme. Certain prior methods of retaining enzymes on a support have also resulted in large increases in apparent $K_M$, the apparent Michaelis constant, indicating a substantial decrease in substrate affinity.

Accordingly, it would be desirable to provide a reactor or device which avoids or minimizes the deficiencies of the prior art and provides a biochemically active enzyme that remains active after being stably retained by a matrix. The bio-artificial organ of the present invention meets the foregoing requirements.

SUMMARY OF THE INVENTION

The present invention is directed to a bio-artificial organ which permits the treatment of an extracorporeal blood flow by an immobilized, biochemically active enzyme, to a method for making such an organ, and to a method of treating patients therewith. The bio-artificial organ generally comprises a reactor housing containing a biochemically active matrix capable of enzymatically acting on a substrate. The biochemically active matrix includes a biochemically active enzyme disposed within a plurality of semi-permeable microcapsules which are entrapped within a gel matrix. Liquid permeability of the active matrix is such as to permit the passage of at least some of the substrate, and also enzyme-substrate reaction products, to and from the enzyme or enzymes that are present within the microcapsules.

The gel matrix can be retained on a physical support means to form a biochemically active member. Alternatively, the gel matrix can be formed (cast) on a solid support and then removed for use. In the organ, the biochemically active matrix can be used alone or in combination with the physical support means. The biochemically active matrix alone, or as a biochemically active member, defines a biochemically active element.

The biochemically active matrix is produced by encapsulating a biochemically active enzyme within microcapsules having a semi-permeable membrane. The microcapsule membrane retains the enzyme while permitting substrate access to the encapsulated enzyme. When the terms "substrate" and "enzyme" are used together or in the same context, these terms have their generally understood biochemical meanings.

The microcapsules containing the biochemically active enzyme are then mixed with a gelable solution to produce a composition which when gelled permits the passage of substrate and enzyme-substrate reaction products. The composition is then spread on a physical support means such as a glass plate and is permitted to gel into a gel matrix with the microcapsules entrapped therein to form a biochemically active member. The term "entrapped", as used herein, denotes that the microcapsules are retained in the gel; i.e., located within the gel; however, portions of microcapsule membrane may be exposed along the surface defined by the gel. The microcapsules can be entrapped within the gel by physical or chemical means as long as the desired permeability of the gel matrix is obtained. The biochemically active matrix can be removed from the physical support means for use in the organ or can remain on the physical support means to serve as a biochemically active member.

To permit the enzyme to react with the substrate, an extracorporeal blood stream or flow is passed over the biochemically active matrix without the enzyme being diffused into the blood stream or flow. Any enzyme useful for the treatment of blood disorders can be used, provided that both the substrate and the enzyme-substrate reaction products are capable of passing through the chosen microcapsule membrane and gel matrix. Such enzymes include urease, asparaginase, beta-glucuronidase, glutaminase, indolyl-3-alkane-α-hydroxylase (a tryptophan degrading enzyme), and the like.

Direct immobilization of an enzyme on the surface of a matrix has certain disadvantages. Immobilization with a linking agent often causes a dramatic change in the apparent $K_M$ (Michaelis constant) of the enzymes indicating a decreased affinity for the substrate. In addition, such immobilized enzymes are often subject to leakage from the surface, as a result of in vivo scission of the covalent bond used to link the enzyme to the matrix. However, these problems are avoided by containing the enzyme within a semi-permeable microcapsule having a permeability such that the enzyme is physically constrained, but without necessarily containing a chemical linkage which may interfere with the affinity of the enzyme for its substrate.

Thus, otherwise toxic, free enzymes, such as asparaginase, can be utilized in immobilized form for their beneficial qualities while otherwise deleterious qualities of the enzymes are minimized or substantially eliminated.

The bio-artificial organ can be prepared, if desired, to contain a plurality of active elements, one or more of which includes different biochemically active enzymes so that more than one enzymatic action can be carried out on the blood stream during its passage through the bioartificial organ. This minimizes the number of extracorporeal passages of blood and time needed to carry out the desired treatment.

The bio-artificial organ of the present invention when containing urease-bearing microcapsules is also useful for reducing the urea content of a patient's blood prior to hemodialysis as well as for reducing the urea content of the dialysis fluid in a dialysis system utilizing a recirculating regenerated dialysate.

Encapsulation within microcapsules provides another important advantage by increasing the "shelf life" of the bio-artificial organ produced. This not only provides for availability of such treatment devices, but also decreases their cost to use.

Numerous other advantages and features of the present invention will become readily apparent in the following detailed description of the invention, the accompanying examples and drawings, and the appended claims.

BRIEF DESCRIPTION OF THE DRAWINGS

FIG. 1 is a schematic representation showing a process used to construct a bio-artificial organ of the present invention having enzyme-containing microcapsules entrapped within a gel matrix;

FIG. 2 is a perspective fragmentary view, showing a bio-artificial organ of the present invention including a reactor housing containing a plurality of physically supported, enzyme-bearing matrices;

FIG. 3 is a graph showing the results of in vivo testing of a urease-red cell ghost organ of the present invention; and FIG. 4 is a set of graphs showing the results of in vitro testing of a urease-red cell ghost organ before and after in vivo exposure.

DETAILED DESCRIPTION OF THE PREFERRED EMBODIMENTS

The present invention relates to a bio-artificial organ which generally comprises a reactor housing containing at least one biochemically active enzyme in discrete microcapsules which are entrapped within a gel matrix such that the passage of substrate and enzyme-substrate reaction products is permitted to and from the enzyme. The microcapsules may be made of a wide variety of semi-permeable materials of natural or synthetic origin. The microcapsules preferably are red cell ghosts, but may also be made of nylon or cellulose acetate hollow spheres, for example. See Chong et al.: "In Vivo Effects of Intraperitoneally Injected L-asparaginase Solution and L-asparaginase Immobilized Within Semi-Permeable Nylon Microcapsules With Emphasis on Blood L-asparaginase, Body L-asparaginase and L-asparaginase Levels." Enzyme, 18:218 (1974).

Red cell ghost microcapsules having entrapped enzymes can be prepared using numerous methods. See Bodemann et al., "Factors Controlling The Resealing of the Membrane of Human Erythrocyte Ghosts After Hypotonic Hemolysis", Membrane Biology, 8:1 (1972), Billah et al., "Permeability Characteristics of Erythrocyte Ghosts Prepared Under Isotonic Conditions by a Glycol-Induced Osmotic Lysis", Biochim. Biophys. ACTA, 465: 515–26 (1977), Zimmermann et al., "Enzyme Loading of Electrically Homogeneous Human Red Blood Cell Ghosts Prepared By Dielectric Breakdown", Biochim. Biophys ACTA: 436: 460–474 (1976).

The red cell ghosts can be made from red cells initially drawn from the patient to be treated, thus increasing the biocompatibility of the organ produced. In the preferred preparation method, blood is withdrawn from a donor and centrifuged so that at least a portion of the plasma can be removed. The red cells are hemolyzed in a solution containing $MgSO_4$ and the enzyme to be contained within the ghosts as is known in the art. After the red cells have been hemolyzed and the enzyme has difused into the red cell ghosts, normotonicity is restored to reseal the red cell ghosts in a manner known to the art.

The red cell ghosts containing enzymes can be fixed so that the enzyme retention within the red cell ghost is enhanced.

Fixation of the enzyme-containing red cell ghosts is typically carried out using an organochemical linking agent, as discussed specifically below for the most preferred linking agent, herein, glutaraldehyde. Several other organochemical linking agents are also useful and are exemplified by dialdehydes containing up to 10 carbon atoms, such as the most preferred glutaraldehyde and teraphthaldehyde, cyanuric chloride, cyclic anhydrides containing 4–8 carbon atoms, such as succinic anhydride, maleic anhydride, and adipic anhydride, activated dicarboxylic acid esters which contain 2–8 carbon atoms in the dicarboxylic acid, such as bis(-salicyl) succinate, bis(3, 5-dibromosalicyl) fumarate, bis(N-hydroxysuccinimido) adipate, and the like, as are known in the art.

As an illustration of fixation of the enzyme-containing red cell ghosts with glutaraldehyde, the ghosts are contacted with a solution containing glutaraldehyde, at a preferred concentration of about 1 to about 2.5 volume percent glutaraldehyde. The contact time is relatively short, usually a single flush of the enzyme-containing red cell ghosts with the glutaraldehyde solution. The solution preferably contains imidazole buffered saline (IBS) i.e. 0.15 M NaCl, 0.02 M imidazole, at a pH value of 7.35.

The fixed red cell ghosts may be stored for several months in a solution of imidazole buffered saline (IBS) containing 0.02 weight percent sodium azide at 4° C. The fixed red cell ghosts can also be cryoprotected by being treated with polyethylene glycol (PEG) and lyophilized.

A variety of polyethylene glycols (PEG) are useful herein for preparing cryoprotected red cell ghosts. In preferred practice, a PEG containing an average of about 12 to about 150 polymerized ethylene oxide units is used. More preferably, the PEG contains an average of about 40 to about 75 polymerized ethylene oxide units. Polyethylene glycols having an average of about 12, 40, 75 and 150 polymerized ethylene oxide units are commercially available from several sources, as are additional polyethylene glycols having average numbers of polymerized ethylene oxide units which lie between the above-mentioned extreme values. A principal criterion useful in selecting a PEG is that it freezes and stays frozen under the conditions of lyophilization (freeze drying).

enzyme-containing red cell ghosts as discussed before, the fixed ghosts are suspended in an aqueous solution containing at least about 5 weight percent PEG. The aqueous solution preferably contains about 5 to about 20 weight percent of the selected PEG, and more preferably contains about 5 to about 10 weight percent of the PEG. The concentration of fixed ghosts in the suspension is preferably about 10 to about 50 percent by weight of the total suspension, and more preferably the concentration is about 30 to about 50 weight percent.

The suspension thus prepared is then lyophilized or freeze-dried, and the cryoprotected red cell ghosts recovered. Typically, lyophilization is carried out by placing the suspension into a vessel which is then, preferably, pre-chilled in a water-ice bath to condition the fixed, suspended red cell ghosts for freezing. Thereafter, the pre-chilled suspension, or a suspension substantially at ambient temperature, is preferably shell-frozen in a vessel suitable for use in lyophilization; the same or different vessels being used for pre-chilling and lyophilization. "Shell-freezing" is a term used in the freeze-drying arts to mean that a liquid is frozen as a layer on the inner surface of the vessel. Shell-freezing provides a larger frozen surface area and therefore a faster rate of freeze-drying than would be obtained if the suspension were merely frozen in a block. Shell-freezing is suitably carried out by rotating the vessel and its contents in a bath of dry ice and a liquid, such as acetone or methanol, or the like which does not, itself, freeze when in contact with the dry ice.

The atmospheric pressure within the vessel containing the frozen suspension is then reduced to no more than about 0.03 atmospheres, and preferably to no more than about 0.015 atmospheres, while the suspension is maintained in a substantially frozen state. The reduced pressure within the vessel is maintained until the red cell ghosts are substantially dry, i.e., the water and other volatile ingredients have been removed. A convenient way to know that the red cell ghosts are substantially dry is to determine the temperature of the outside surface of the vessel since once substantially all of the volatiles are removed from the vessel, the outside surface of the vessel will return to the temperature of the surrounding area, i.e., ambient temperature. Once the cryoprotected red cell ghosts are dry, the pressure within the vessel is returned to atmospheric, and the dried, cryoprotected red cell ghosts are thereafter recovered.

Biochemically active enzymes suitable for present purposes can also be microencapsulated within a synthetic sheath of controlled permeability using techniques such as mechanical microencapsulation, coacervation, interfacial polymerization, liquid-liquid phase separation, and the like as long as the processing conditions are sufficiently mild to avoid a substantial denaturization or deactivation of the desired enzyme.

The foregoing techniques are known in the art, but will be described herein briefly in the interests of completeness.

In particular, mechanical microencapsulation involves the spray drying and impingement of an aqueous, enzyme-containing microcapsule core material on biocompatible, hardenable films of polymeric microcapsule wall material having the desired permeability. Coacervation is the technique which relies on the ability of an aqueous solution of a colloid to separate into two liquid layers, one richer in colloid solute than the other, depending on the colloid concentration of the system, the solvent and temperature of the system, and/or the absence or presence of an electrolyte or a polyelectrolyte within the system. To microencapsulate, a liquid, wall-forming polymer concentrate (coacervate) is formed as a separate phase entity of an initial solution of the semi-permeable wall-forming polymer and surrounds the enzyme-containing microcapsule core material that is dispersed as another distinct phase in the initial solution.

Interfacial polymerization to produce semi-permeable, enzyme-containing microcapsules entails polycondensation between two relatively fast-reacting polymer intermediates present in two immiscible liquid phases. One of the intermediates is present as a constituent of the aqueous, enzyme-containing microcapsule core material dispersed as a discontinuous phase in a continuous liquid phase vehicle which contains the other of the polycondensation intermediates.

The liquid-liquid phase separation technique entails the use of a continuous liquid phase vehicle having dissolved therein a potentially semi-permeable wall-forming polymeric material, and a discontinuous phase of minute entities of aqueous, enzyme-containing microcapsule core material dispersed in the vehicle. The wall-forming polymeric material is selected so as to preferentially wet the dispersed core material containing the desired enzyme and is caused to separate out from the continuous liquid phase vehicle (a) by temperature adjustment, (b) by the introduction of another compatible polymer into the vehicle, which polymer causes the wall-forming polymeric material to come out of the solution, (c) by the introduction of a non-polymeric, non-solvent into the vehicle, thereby decreasing the solubility of the wall-forming polymeric material in the vehicle, and (d) by a combination of two or more of the foregoing steps.

Specific examples of techniques that can be used to produce enzyme-containing microcapsules with microcapsule wall membranes of controlled permeability are disclosed in U.S. Pat. No. 3,674,704 to Bayless et al., U.S. Pat. No. 4,107,071 to Bayless, U.S. Pat. No. 3,748,277 to Wagner, and U.S. Pat. No. 3,415,758 to Powell et al. and are incorporated herein by reference.

The microcapsules, e.g., the enzyme-bearing red cell ghosts, are then mixed with a gelable solution to form a composition which is spread on a physical support means such as a roughened glass plate. The glass plate can be roughened with hydrofluoric acid or sandblasting as is known in the art. FIG. 1, Diagram A shows such a roughened glass plate 12 before it is covered with the composition. The term "solution" is to be understood as including both true solutions and suspensions. The composition is then gelled to form a biochemically active matrix on the physical support means. The active matrix and the physical support means are collectively referred to as a biochemically active member.

Preferably, the gelable solution is a polysaccharide solution and optimally is an agarose solution which irreversibly solidifies below about 40° C. One such agarose is that designated as "Low Gel Temperature Agarose" available from Bio-Rad Laboratories of Richmond, California; this agarose irreversibly gels at about 37° C. In addition to agarose, other polysaccharides such as cross-linked heparin, cross-linked mucopolysaccharides, as well as polymers of neutral sugars may be used to prepare the gelable solution.

FIG. 1, Diagram B shows the agarose gel 14 matrix entrapping red cell ghosts 16 which contain biochemically active enzymes represented in the Diagram by dots. The red cell ghosts can also be further retained within the gel matrix by cross-linking with a linking agent such as glutaraldehyde. This is represented in FIG. 1, Diagram C, by cross-linking agent 18. This cross-linking can be accomplished contacting, as by flushing the gel covered plate with a solution containing about one to about two percent glutaraldehyde.

As shown in FIG. 2, a plurality, in this case twenty, biochemically active members 22, which include glass plates 23 can be removably fixed as by being inserted into slots (not shown), within a reactor housing 24. The reactor housing 24 has an inlet 26 and an outlet 28 to permit an extracorporeal blood flow to be passed over the matrix carried by the glass plates 23. The inner surfaces of the reactor housing 24 should be made of a material which is compatible with an extracorporeal blood flow.

Any convenient size of physical support means can be utilized. In one particularly preferred embodiment of this invention, glass plates having roughened surfaces were used which had dimensions of about 10×10×0.1 centimeters. In this embodiment the plates were first cleaned with nitric acid and then coated with a solution of agarose, 0.5 weight percent, (Elphor coating procedure), as is conventionally used to prevent clotting by blood exposure to glass. The surface of the glass plates comprising the physical support means was roughened, as by sand blasting, etching or the like, so that the adhesion of the agarose coating to the glass is enhanced. The agarose coating can also serve as a "primer" coat to assist adherence of the matrix to the glass. It is to be understood that the agarose used for the coating may be different than the agarose used in preparing the gel matrix. A particularly preferred coating can be prepared from a dilute solution of agarose (SeaKem, e.g., 0.5 percent by weight in water. SeaKem is a trade designation for an agarose powder available from Marine Colloids, Inc., Rockland, Me.

In addition to the glass, the physical support means can be made from a variety of relatively inert materials. Examples of such materials include, but are not limited to, metals such as stainless steel and plastic such as poly(ethylene), poly(propylene), copolymers of ethylene and propylene alone or with additional monomers such as vinyl acetate, fluorinated polyolefins such as poly(tetrafluoroethylene), and the like as are used in the medical implant arts.

Specific examples are the polyethylene polymers sold under the trademark designation MICROTHENE MN 718 and MICROTHENE MN 786 sold by U.S. Industrial Chemicals Company. Illustrative homopoly(propylene) polymers useful herein include the polymer sold by Eastman Chemicals under the trade designation 4250G and that material sold by Hercules, Inc. under the designation 6301. An example of an ethylene-propylene thermoplastic elastomer useful herein is that material sold by Exxon Chemical Co., U.S.A. under the designation Vistalon-702. A preferred ethylene-vinyl acetate copolymer is sold under the trademark designation MICROTHENE MU 763. The criteria for the physical support means are that it be capable of supporting the gel matrix, and be compatible, either as is or after suitable treatment, with the other components of the active member and the extracorporeal blood flow.

Preferably, glass plates having roughened surfaces (10×10×0.1 centimeters) are used as the physical support means in the production of the biochemically active member.

Preferably, the agarose, which irreversibly gels below 40° C., is prepared in a solution of imidazole buffered saline, (IBS; 4 percent weight in volume) and heated to about 80° C. The solution is then cooled to about 40° C. or any other suitable temperature above the irreversible gelation temperature for the solute, but below that which could cause enzyme deactivation. A suspension, preferably containing about 50 weight percent enzyme-filled red cell ghosts in a solution of IBS is then also warmed to a temperature above the irreversible gelation temperature of the agarose, such as about 40 degrees C. About 100 to about 200 milliliters of the agarose solution are then mixed with about 100 to 200 milliliters of the red cell ghost suspension. The preferred ratio is about 1:1 to about 2:1 milliliters of agarose solution to each milliliter of red cell ghost suspension to produce a suitable composition.

The produced composition is then spread on a physical support means to form a coating thereon with preferably about one milliliter of the produced composition for each ten square centimeters to be covered. The physical support means is preferably prewarmed to about the temperature of irreversible gelation, such as 37° C. The physical support means can be maintained at this temperature by placing it in a heated water bath with the surface of the support means being just out of the water bath. After the composition has gelled (usually in about 10 minutes), the reverse side of the physical support means can be coated by the same process. Alternatively, both sides of a physical support means can be coated by dipping them into an ungelled composition.

Red cell ghosts have certain particular advantages in bio-artificial organs. High matrix activity is possible in such organs because the volume of the red cell ghosts can comprise about 25 percent of the produced composition. The use of the patient as a donor for the red cells in the preparation of red cell ghosts also provides immunocompatibility. The red cell ghosts also have "ultrathin" membranes of about 400 Angstroms in thickness resulting in short diffusion times. The ghost membrane, because of its selective permeability, can be used to a particular advantage by making use of a preferential uptake of one substrate over another. See Schmer et al., Trans. Am. Soc. Artif. Intern. Organs, XXVI:129 (1980) and Schmer et al., Int. J. Artif. Organs 4:96–101 (1981), both incorporated herein by reference.

Because of the design of the present invention, any one of numerous enzymes can be used such as glutaminase, urease, L-asparaginase beta-glucuronidase and the like. The use of microcapsules such as red cell ghosts is particularly valuable with enzymes which lose substantial biochemical activity when covalently bonded to a support matrix. This is particularly true with the tryptophan degrading enzyme indolyl-3-alkane-$\alpha$-hydroxylase. The bio-artificial organ produced not only showed effective reaction with of the substrate, but also demonstrated no detectable amounts of enzyme leakage.

EXAMPLE 1: UREASE-RED CELL GHOST FREEZE DRYING

Biochemically active microcapsules were produced by using red cell ghost containing urease. Initially, 4.5 milliliters of blood was drawn from healthy donors into plastic tubes containing 0.5 milliliters of 0.1 M sodium citrate. The samples were spun down at 1500×g for about 10 minutes and the plasma with the buffy coat was removed. The cells were washed by being resuspended in the original volume of liquid with a solution of 0.15 NaCl, 0.02 M IBS, pH 7.35. This suspension was tilted several times, and again centrifuged at 1500×g for about 10 minutes. This wash procedure was carried out 5 times at room temperature (20°–25° C.)

The obtained, packed red cells were then cooled down in an ice water bath to 0° C. and hemolyzed with approximately 6 volumes of a solution containing 4 mM $MgSO_4$, 0.02 M TRIS-HCl (pH 7.4) and urease (100 International Units per milliliter of solution; precooled to 0° C. before being added to the red cells). Urease was prepared from Jack Bean meal using 100 grams Jack Bean meal plus 400 milliliters saline dialyzed overnight at 4° C. against 30 volumes of phosphate buffered saline, pH 7.35. See Summer, J. Biol. Chem 69:435 (1926). After about five minutes of gentle shaking in the ice bath, normotonicity was restored by adding 8.5 milligrams NaCl per milliliter of hemolyzing solution. The sample was then transferred to a water bath (37° C.) for 60 minutes. This resealed the red cell ghosts with urease contained within. The resealed red cell ghosts were washed 6 times with a tenfold excess of 0.15 M NaCl, 0.02 M TRIS-HCl (pH 7.4) at room temperature and centrifuged at 1500×g for 10 minutes. After the final wash the supernatant was checked and found to have no residual urease activity. The urease-filled red celled ghosts produced in the foregoing manner were used also in Example 2, below.

One volume of IBS solution containing 2.5 volumne percent glutaraldehyde was rapidly added to one volume of packed, urease filled red cell ghosts, thrice washed with saline, and mixed for 30 seconds using a vortex mixer at room temperature. This fixed the suspended red cell ghosts. The glutaraldehyde fixed red cell ghost suspension was then poured into five volumes of a buffered solution consisting of 0.05 TRIS-HCl, 0.05 M sodium barbital and 0.05 M glycine (pH 7.35) at room temperature and reacted for one hour to neutralize the excess glutaraldehyde. The fixed red cell ghosts were spun down in a Sorbal 2B refrigerated centrifuge at 13,000×g for 5 minutes and washed three times with cold saline.

2–3 Milliliters of the packed red cell ghost layer obtained after the final wash was suspended in 2–3 milliliters of IBS solution (pH 7.35) containing 5–10 weight percent polyethylene glycol (PEG-4,000; available from Union Carbide) to provide cryoprotection. The red cell ghost suspension was cooled to temperature 0° C. on ice water, and thereafter shell frozen in an acetone-dry ice mixture for lyophilization. Lyophilization was carried out at the following conditions.

Enzyme activities were tested before and after lyophilization and after freeze drying by adding distilled water to the lyophilizate to return it to its original volume. Red cell ghosts in a 5–10 percent PEG-4,000, IBS solution without prior fixation with glutaraldehyde and glutaraldehyde fixed red cell ghosts in IBS alone in the absence of PEG-4000 were lyophilized as controls.

Table I shows the successful lyophilization of cryoprotected, glutaraldehyde-fixed urease-red cell ghosts in contrast to cryoprotected non-fixed red cell ghosts and non cryoprotected cells. The cryoprotected-fixed cells (A) lyophilized in the presence of PEG-4000 retained about 50 percent of their original activity. A total loss of activity in the cell layer was observed with cryoprotected non fixed cells (B) and fixed, non PEG cryoprotected cells (C). For each, enzyme was found in the supernatant after reconstitution with the distilled water to the original volume. Free urease, itself, lost about one-half of the activity when lyophilized in 5–10 percent PEG-4000 in the absence of red cell ghosts. Also shown in Table I are the results for red cell ghosts containing indolyl-3-alkane-α-hydroxylase which were prepared in the same manner as the urease red cell ghosts.

TABLE 1

| Enzyme Activity Distribution of Reconstituted Lyophilized Enzyme-Filled Red Cell Ghosts | | | | |
|---|---|---|---|---|
| Enzyme Within Ghosts | Suspension Position After Reconstitution | Percent of Original Activity | | |
| | | A | B | C |
| UREASE | Cell Layer | 50 | 0 | 0 |
| | Supernatant | 0 | 50 | 50 |
| INDOYL-3-Alkane-α-Hydroxylase | Cell Layer | 70 | 0 | 0 |
| | Supernatant | 0 | 70 | 70 |

A = lyophilized in 5–10 percent PEG, glutaraldehyde fixation
B = lyophilized in 5–10 percent PEG, no glutaraldehyde treatment
C = lyophilized after glutaraldehyde treatment, no PEG.

The above results illustrate the protection to freeze-drying afforded to the ghosts by treating the enzyme-filled ghosts with polyethylene glycol after fixation. While urease lost substantially the same relative amount of activity when lyophilized free in the PEG solution, or under conditions A, B, or C, above, only the fixed, cryoprotected, urease-filled ghosts survived with substantial activity so as to be useful after drying and reconstitution.

EXAMPLE 2: UREASE-RED CELL GHOST ORGAN

Urease-filled packed red cell ghosts were prepared as described above in Example 1, above. After the final wash and centrifugation of the enzyme-filled red cell ghosts in physiological saline, the red cell ghost layer was rapidly mixed at room temperature for 30 seconds with the same amount of 2 volume percent glutaraldehyde (Sigma, reagent grade) in IBS pH 7.35. This fixed the red cell ghosts and provided improved strength to the membrane. The suspension was then mixed with 10 volumes of a solution containing 0.05 M TRIS-HCl, 0.05 M sodium barbital and 0.05 M lysine pH 7.4 to neutralize excess glutaraldehyde. These fixed red cell ghosts were completely impermeable to entrapped hemoglobin and preserved their enzyme activity for several months. The fixed red cell ghosts were stored at 4° C. in a solution of IBS containing 0.02% sodium azide as a preservative.

100 Milliliters of an aqueous IBS solution containing 4 weight percent by volume of low temperature agarose (commercially available as "Low Gel Temperature Agarose" from Bio-Rad Laboratories of Richmond, Calif.) was heated to 80° C. and then cooled to 40° C. This agarose irreversibly gels below 37° C. and provides a means for gently entrapping the red cell ghosts containing enzymes. 100 Milliliters of suspension containing 50 weight percent urease-filled red cell ghosts in IBS was prepared and warmed to 40° C.

The agarose solution and red cell ghost suspension were then combined and mixed for 5 minutes (at 38°–40° C.) to form a composition. Roughened glass plates (10×10×0.1 cm) were cleaned in nitric acid and coated with a solution of 0.5 percent agarose (Elphor coating procedure) to prevent clotting by blood exposure to glass. The plates were prewarmed by placing them on an adjustable table with the plane of the table just reaching out of the water surface in a 37° C. waterbath. 10 Milliliter aliquots of the obtained composition were spread on the roughened glass plates. The composition, containing the fixed, urease-filled red cell ghosts, solidified in about 10 minutes when placed at a 22° C. surrounding. The reverse side of the glass plates were then similarly coated.

Twenty such plates were fixed within a cubical reactor housing having an inlet and an outlet to accomodate an extracorporeal blood flow. The reactor housing was made of Polyacrylic amide and had side dimensions of about 13×13 cm. Two substantially identical artifical organs were constructed in the foregoing manner. The produced bio-artificial organs were filled with a solution of IBS containing 0.02 weight percent sodium azide, sealed and stored.

In Vivo Testing

Animal experiments were carried out on healthy, fully heparinized sheep with carotid-jugular shunts. The extracorporeal blood stream entered the artificial organ from below. Concentrated urea (3.3 mM was delivered by a pump into the blood stream at a rate of 200 milligrams per minute. The blood flow rate was 200 milliliters per minute. At the venous (outlet) end, samples were taken for ammonia determination and platelet count. In vivo clearance of urea was determined by measuring the residual urea at the venous end of the organ by enzymatic conversion with urease and Nessler determination of the resulting ammonia increase, after deproteinization of the obtained plasma by trichloroaceteic acid. No major consumption of platelets was observed during two experiments with the same urease red cell ghost organ.

FIG. 3A graphically shows the results of three experiments with the same organ using three different modes of urea infusion. In the first experiment (I) constant urea infusion forced determination on the experiment after one hour due to toxic reactions in the animal (Hyperammonemia). In the second experiment (II) urea was infused at the beginning of each hour for only 5 minutes. In the third experiment (III) urea was infused for five minutes at the beginning of the experiment and at Hour 5 of the experiment. FIG. 3B reflects a composite of the results of three other experiments with the second reactor. Urea was infused five minutes at the beginning of the experiment and at Hour 5 of the experiment. While urea entered the red cells rapidly, only a slow release of ammonia from the ghosts was observed. The artificial organ showed an effective clearance of urea in vivo. From 3.3 mM urea (200 mg) infused per minute (short-term infusion) only 0.3 mM could be determined at the venous end, indicating a clearance of 3.0 mM urea per minute.

In Vitro Testing

Before and after each exposure of the organs to an extracorporeal blood flow, maximal enzyme activity was measured by the conversion of urea (25 mM in phosphate buffered saline, PBS) to ammonia, ammonia determination by Nesslerization. See Roberts, et al., J. Biol. Chem. 247:84 (1972). One liter of urea solution was cycled through the organ at room temperature at a flow rate of 200 milliliters per minute. Ammonia was determined every 15 minutes for 45 minutes.

FIG. 4 shows the results of in vitro testing of the urease-red cell ghost organ before (0) and after (I, II, III) each in vivo exposure. As can be seen in FIG. 4, no loss in enzyme activity in the organ was observed even after a total of 15 hours of in vivo exposure. No leakage could be detected from the gel matrix after in vivo exposure to a detection limit of 0.5 percent red cell ghost leakage/hour.

$K_M$ determinations were carried out at room temperature on substrate solutions ranging from 25 mM to 0.025 mM in 1,000 milliliters phosphate buffed saline (PBS) pH 7.4 using the total organ. Data were plotted according to Lineweaver and Burk. See Christensen et al. *Enzyme Kinetics* W. B. Saunders Co., 1967 pp. 68–91. The urease-red cell ghost organ $K_M$ apparent was $1.0 \times 10^{-2}$ and thus showed only a moderate increase of $K_M$ apparent as compared to the free enzyme $K_M$ of $3 \times 10^{-3}$. Shelf life was determined by weekly testing of the constructed organs every week for up to 12 weeks under V max conditions outlined above. No enzyme activity loss could be observed during this period.

The urease filled red cell ghost organ proved effective for the reduction of urea in solution, both during in vitro and in vivo tests. The agarose used not only provided stable gel for entrapping the red cell ghosts, but also permitted the transfer of urea, and dissolved ammonia and carbon dioxide to and from the red cell ghosts. The lack of detectable leakage of red cell ghosts and the continued enzyme activity after 15 hours of in vivo points to the excellent physiochemical stability of the system.

The foregoing specification is intended as illustrative and is not to be taken as limiting. Still other variations within the spirit and scope of this invention are possible and will readily present themselves to those skilled in the art.

What is claimed:

1. A biochemically active matrix suitable for use in bio-artificial organ comprising at least one biochemically active enzyme disposed within a plurality of semi-permeable microcapsules which are entrapped within a gel matrix, the gel matrix and microcapsule each having a permeability such that the substrate and enzyme-substrate reaction products pass to and from the microencapsulated enzyme.

2. The biochemically active matrix of claim 1 wherein the microcapsules are red cell ghosts.

3. The biochemically active matrix of claim 1 wherein the microcapsule wall is made of a synthetic material.

4. The biochemically active matrix of claim 1 wherein the biochemically active enzyme is urease.

5. The biochemically active matrix of claim 1 wherein the gel matrix is formed of a polysaccharide.

6. The biochemically active matrix of claim 5 wherein the gel matrix is formed of an irreversibly gelled agarose.

7. The biochemically active matrix of claim 6 wherein the agarose has a temperature of irreversible gelation of about 37° C.

8. A biochemically active matrix for use in a bio-artificial organ comprising: a biochemically active enzyme disposed within a plurality of red cell ghosts which are entrapped within an agarose gel having a permeability such that substrate and enzyme-substrate reaction product can pass and to from the enzyme.

9. A bio-artificial organ comprising, in operative combination:

(a) a reactor housing defining an enclosed space, an inlet and an outlet, and the inner surface of the reactor being of material compatible with an extracorporeal blood flow;

(b) a gel matrix within the reactor housing;

(c) a plurality of semi-permeable microcapsules entrapped within the gel matrix; and (d) a biochemically active enzyme disposed within the microcapsules;

the gel matrix and the microcapsules each being permeable to substrate and enzyme-substrate reaction products.

10. A bio-artificial organ of claim 9 wherein the gel matrix is formed of an agarose which irreversibly gels at a temperature of about 37° C.

11. The bio-artificial organ of claim 9 wherein the microcapsules are red cell ghosts.

12. The bio-artificial organ of claim 9 wherein the gel matrix is disposed on a physical support means positioned within the reactor housing.

* * * * *

UNITED STATES PATENT AND TRADEMARK OFFICE
CERTIFICATE OF CORRECTION

PATENT NO. : 4,431,428
DATED : February 14, 1984
INVENTOR(S) : Gottfried Schmer

It is certified that error appears in the above-identified patent and that said Letters Patent is hereby corrected as shown below:

Col. 4, line 67, before "enzyme-containing" insert -- After preparing and fixing the biochemically active --.

Signed and Sealed this

Twenty-sixth Day of June 1984

[SEAL]

Attest:

Attesting Officer

GERALD J. MOSSINGHOFF

Commissioner of Patents and Trademarks